United States Patent
Stahl et al.

(10) Patent No.: US 6,576,251 B1
(45) Date of Patent: Jun. 10, 2003

(54) CARBOHYDRATE MIXTURE

(75) Inventors: Bernd Stahl, Friedrichsdorf (DE); Gunther Sawatzki, Munzenberg (DE)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 09/341,775

(22) PCT Filed: Jan. 16, 1998

(86) PCT No.: PCT/EP98/00234

§ 371 (c)(1),
(2), (4) Date: Nov. 9, 1999

(87) PCT Pub. No.: WO98/31241

PCT Pub. Date: Jul. 23, 1998

(30) Foreign Application Priority Data

Jan. 16, 1998 (DE) .......................................... 197 01 382

(51) Int. Cl.$^7$ .................... A61K 47/36; A61K 31/7004; A61K 31/702; A61K 31/715
(52) U.S. Cl. ........................... 424/439; 514/23; 514/25; 514/53; 514/54; 514/58; 514/61
(58) Field of Search .............................. 514/23, 25, 53, 514/54, 58, 61; 424/439

(56) References Cited

U.S. PATENT DOCUMENTS 4,762,822 A * 8/1988 Ettinger ....................... 514/25
5,849,324 A * 12/1998 Dohnalek et al. ............ 424/440
6,045,854 A * 4/2000 Prieto et al. ................. 426/801

FOREIGN PATENT DOCUMENTS

| DE | 39 35 906 A | 5/1991 |
| WO | WO 92 10947 A | 7/1992 |
| WO | WO 94 18986 | 9/1994 |

* cited by examiner

Primary Examiner—James O. Wilson
Assistant Examiner—Leigh C. Maier
(74) Attorney, Agent, or Firm—Bacon & Thomas

(57) ABSTRACT

The invention relates to a carbohydrate mixture for dietetic foods administered by the enteral or parenteral route and pharmaceuticals, characterized in that said mixture consists of (a) monosaccharide(s), (b) oligosaccharide(s) (at most hexasaccharides) and (c) polysaccharide(s) (at least heptasaccharides), where the mixing ratio a, b, c, in respect of weight, is: $\alpha=1$, b=40 to 1000, and c=1 to 50, and in that it contains at least 1 weight percent of fucose occurring either freely and/or bound to an oligosaccharide and/or a polysaccharide. According to the invention, the carbohydrate mixture has both a nutritional and a biological effect which is considerably greater than the corresponding action of the individual constituents.

16 Claims, No Drawings

CARBOHYDRATE MIXTURE

The invention concerns a carbohydrate mixture for dietetic, enteral and parenteral foods and also pharmaceuticals, and the use of this carbohydrate mixture.

As is well-known, carbohydrates are one of the essential basic pillars of the diet. Hence, a great diversity of carbohydrates are added to the a great variety of foods, in particular "artificially" produced foods, and also pharmaceuticals. The purpose of the carbohydrates here is primarily of a nutritive nature, or they function as dietary fibre.

The carbohydrates consist of monosaccharides, or are composed of these. Depending on degree of polymerisation, the carbohydrates are described as oligosaccharides or polysaccharides or glycans. In the context of the present documents, carbohydrates with up to 6 monosaccharide units are understood here as oligosaccharides. Carbohydrates with 7 and more monosaccharides are referred to here as polysaccharides.

Owing to the variability of the monomers making up the carbohydrates, the position of the glycosidic bond and the anomerism of the carbohydrates, these carbohydrates and conjugates thereof constitute an extremely heterogeneous and extensive class of substances.

Now carbohydrates have a great diversity of biological functions. In this connection, purely by way of example, it is mentioned that glycan structures play an important part particularly in cell-matrix, cell-cell and similar recognition and adhesion processes. The carbohydrate structures are present both as free oligosaccharides and also in bound form, for example in glycoproteins, proteoglycans and glycolipids. The adhesion of microorganisms to glyco-structures of epithelia/endothelia or other endogenous cells inter alia also has effects on the cell metabolism of the host organism. Now the list of functions that are performed by carbohydrates could be extended to any length. The above-described function of the glycan structures is thus only an arbitrarily chosen example.

Carbohydrates are now used increasingly in foods, "functional food" and pharmaceuticals with a biological activity in mind. Previously, however, only some specific carbohydrate species possessing a particular property were used.

Hence the purpose of the present invention is to provide a carbohydrate mixture which can be incorporated into dietetic, enteral and parenteral foods and also pharmaceuticals, and as well as a nutritive effect also possesses a broad spectrum of activity.

This purpose is achieved through the teaching of the claims.

It was surprisingly found that the biological action of the mixture of monosaccharides, oligosaccharides and polysaccharides according to the invention is considerably more potent than the corresponding action of the individual components. Thus with the mixture according to the invention the following biological effects can be achieved:
  prevention of the adhesion of pathogenic substances/
    organisms such as toxins, viruses, bacteria, fungi, transformed cells and parasites
  decomposition of complexes of toxins, viruses, bacteria, fungi and other pathogens with endogenous cells and their elimination from the body
  stabilisation of a natural microflora
  acceleration of wound-healing (for pharmaceutical and enteral mixtures).

Thus the mixture according to the invention is suitable for the prophylaxis and/or treatment of symptoms/diseases, which are connected with the association/adhesion of the said substances and organisms to epithelia or other endogenous cells (such as diarrhea, meningitis, otitis, gastritis and influenza). The mixture according to the invention additionally has a nutritive effect owing to degradation reactions by endogenous enzymes and subsequent absorption of the products.

While the degradation rate, kinetics and absorption are relevant for the nutritive and prebiotic effects of the carbohydrate mixture according to the invention, surprisingly not only the chemical composition but also the mixing ratio of monosaccharides/oligosaccharides/poly-saccharides is important for the biological function.

Thus, the mixing ratio of a=monosaccharide, b=oligosaccharide and c=polysaccharide according to the invention is as follows: a=1, b=40 to 1000, c=1 to 50.

As oligosaccharides here, those up to hexasaccharide (e.g. mono-, di-, tri-, terra-, penta and hexasaccharide) are understood.

When in the context of the present documents a saccharide is referred to in the singular, then this can be not only a single species, but also a mixture of any species. When in addition in the context of the present documents ranges are referred to, then with the statement of the range at least all whole-number intermediate values and also narrower ranges included by the range are covered and disclosed. This means for example for the component c, which can be 1 to 50, that with this the intermediate values, such as 2, 3, 4, . . . 12, 13, 14, . . . 25, 26, 27, . . . 37, 38, 39, 40, 41 . . . are also covered. The same applies analogously for the component b, so that with this all, at least whole-number, intermediate values lying between 40 to 1000 (e.g. 41, 42, 43, 44 . . . up to 998, 999) are disclosed.

The mixture of the components of the carbohydrate mixture according to the invention thus constitutes an essential feature of the invention. The mixing ratio of monosaccharides, oligosaccharides and polysaccharides here is preferably 1:40:10 to 1:1000:1 and in particular 1:80:20. In this case also, by this statement, all, particularly whole-number, values lying between the range limits are also covered and disclosed. Here the molecular weight of the polysaccharides can be extended to several Mda and to particular carbohydrates with a large number of active groups.

A further important feature of the mixture according to the invention consists in that at least ca. 1 wt % fucose is present in this mixture (incidentally, unless otherwise stated, all quantity statements are based on weight). Here the fucose can be present in free form or in bound form (as fucosylated oligosaccharide or fucosylated polysaccharide). Naturally, it is also possible that the facose is present both in free form and also in bound form. Here this facose preferably makes up at least ca. 5 wt % and in particular 5 to 10 wt % of the carbohydrate mixture according to the invention.

According to a further preferred embodiment, the carbohydrate mixture according to the invention in addition contains ca. 1 wt % sialic acid Here in the context of the present documents the term sialicacid stands for the following substances or the following substances are subsumed thereunder: N-acetyl-neuraminic acid, N-glycolyl-neuraminic acid and other neuraminic acids. All these sialic acids can also be present in O-acetylated form. Here the sialic acids can be present free or be bound to an oligosaccharide and/or to a polysaccharide. Naturally, any mixtures are also possible. Here the sialic acid preferably makes up 1 to 5 wt % and is present especially as sialyllactose and/or disialyllactose or disialyllacto-N-tetraose.

For the production of the carbohydrate mixture according to the invention, all carbohydrates and carbohydrate mixtures previously known and in particular used for the production of foods or foodstuffs can be used. It is also possible to use raw materials already altered by technical modification The production of the mixture according to the invention can be effected by simple mixing of the appropriately selected monosaccharides, oligosaccharides and polysaccharides in the desired mixing ratio.

Thus as raw materials both free carbohydrates such as storage carbohydrates (starch, fructans) and also structural carbohydrates such as celluloses, hemicelluloses and chitins can be used. In addition, glycoconjugates such as glycolipids, glycoproteins, proteoglycans, etc., can be used. It is also possible to perform tan enzymatic modification of the raw materials and products with hydrolases (for example, glycosidases, transglycosidases and lipases), transferases (for example fucosyl-transferases and sialyltransferases), isomerases (for example aldolases and ketolases), oxidoreductases (for example oxidases) and reductases (glucose dehydrogenase)), lyases (for example polysaccharide lyase) and ligases. Further, it is possible to perform a technical modification of the raw materials and products, namely by pressure (for example extrusion), temperature (for example caramelisation), organic syntheses, organic modification (for example carboxymethylation and peracetylation), acid and/or basic hydrolysis and fractionation (for example on the basis of size and/or physicochemical parameters such as charge and hydrophobicity).

Also, the carbohydrate mixture according to the invention is essentially composed of the monosaccharides listed below and the oligosaccharides and polysaccharides built up from them:

N-acetyineuramninic acid, N-glycolylneuraminic acid and/or O-acetylated forms thereof, D-glucose, D-fructose, D-galactose, D-mannose, L-fucose, D-N-acetylglucosarnine, D-N-acetl-galactosamine, D-xylose, L-rharnnose, D-arabinose, D-allose, D-talose, D-idose, D-ribose and monosaccharides with carboxyl groups such as D-galacturonic acid.

These monomers and the higher units based on them can also be modified by -$OSO_3H$ and/or $OPO_3H$ groups.

Here the fucosylation or sialisation of the carbohydrates can be performed in the usual way.

As already stated above, the mixture ratio a:b:c can be up to 1:1000:1. This is in particular the case when only little free fucose and/or free sialic acid is present.

The ratio of the total neutral carbohydrates to the total acid carbohydrates (for example NeuAc and/or carbohydrates with $OSO_3H$ and/or $OPO_3H$ groups should preferably be 00:1 to 1:1, and especially preferably 10:1.

The monosaccharides and oligosaccharides used in the mixture according to the invention admittedly show a low affinity (binding or complexing) for certain receptors, but owing to the increased diffusion and flexibility can surprisingly decompose already existing complexes of substances and organisms (toxins/viruses, bacteria and cells) with the target structures (for example epithelial surfaces) and the recognition molecules associated therewith (i.e. receptors).

The polysaccharides present in the mixture according to the invention display many epitopes (binding sites) and hence possess an affinity several orders of magnitude higher and hence strong binding (compared to the small molecules) to the corresponding receptors. In addition, though molecules with such polyvalent binding sites, a cross-linking of many recognition molecules is achieved. Thus these polysaccharides can stably mask substances and organisms, for example bacteria, but in some circumstances also their receptors and all (epiihelial) surfaces. Adhesion of the substances and organisms, for example bacteria, to cell surfaces and all the epithelia is thus prevented. In addition, the exclusion or the destruction of the substances and organisms from the body is furthered.

The fucose and sialic acid units influence the biological activity of oligo- and polysaccharides.

Below, various carbohydrate mixtures representing preferred embodiments are described. In this, statements are based on wt %, unless otherwise stated.

EXAMPLE 1

| Composition | |
|---|---|
| Component | Wt % |
| Fucose | 0.5 |
| Glucose | 0.5 |
| Sialyllactoses | 1 |
| Fucosyllactoses | 0.5 |
| Fucosylated oligosaccharides such as Lactofucopentaoses | 4 |
| Sialylated oligosaccharides such as Disialolacto-N-tetraose | 1 |
| Maltodextrin | 72.5 |
| Starch | 20 |

EXAMPLE 2

| Composition | |
|---|---|
| Component | Wt % |
| Fucose | 0.5 |
| Glucose | 0.5 |
| Sialyllactoses | 1 |
| Fucosyllactoses | 0.5 |
| Fucosylated oligosaccharides such as Difucosyl-lactose | 4 |
| Sialylated oligosaccharides such as Sialolacto-N-hexaoses | 1 |
| Inulin | 72.5 |
| Starch | 20 |

EXAMPLE 3

| Composition | |
|---|---|
| Component | Wt % |
| Fucose | 1.5 |
| Glucose | 0.5 |
| Sialyllactoses | 1 |
| Fucosyllactoses | 0.5 |
| Fucosylated oligosaccharides such as Difucosyl-lacto-N-tetraose | 3 |
| Sialylated oligosaccharides such as Disialolacto-N-hexaoses | 1 |
| Oligosaccharides such as mannans and Galactans | 10 |
| Inulin | 62.5 |
| Microcrystalline cellulose | 20 |

EXAMPLE 4

| Composition | |
|---|---|
| Component | Wt % |
| Fucose | 1.5 |
| Glucose | 0.5 |
| Sialyllactoses | 1 |
| Fucosyllactoses | 0.5 |
| Fucosylated oligosaccharides such as Lactofucopentaoses | 3 |
| Sialylated oligosaccharides such as | |
| Disialolacto-N-tetraose | 1 |
| Galactooligosaccharides | 10 |
| Inulin | 62.5 |
| Microcrystalline cellulose | 20 |

EXAMPLE 5

| Composition | |
|---|---|
| Component | Wt % |
| Fucose | 0.1 |
| Glucose | 0.5 |
| Sialyllactose | 0.5 |
| Fucosyllactoses | 4.9 |
| Disialolacto-N-tetraose | 2.0 |
| Maltodextrin | 70 |
| Starch | 22 |

EXAMPLE 6

| Composition | |
|---|---|
| Component | Wt % |
| Fucose | 0.1 |
| Glucose | 0.5 |
| Sialyllactose | 1 |
| Fucosyllactoses | 0.9 |
| Galacto-oligosaccharides | 20.5 |
| Inulin | 5 |
| Starch | 72 |

What is claimed is:

1. Carbohydrate mixture for dietetic, enteral and parenteral foods and also pharmaceuticals,
characterised in that
it is made up of a=monosaccharide(s), b=oligosaccharide(s) having 2 to 6 monosaccharide units and c=polysaccharide(s) having 7 or more monosaccharide units with a mixing ratio a:b:c, based on weight,
a=1
b=40 to 1000 and
c=1 to 50, and
contains at least 1 wt % fucose in free form and/or in a form bound to an oligosaccharide and/or a polysaccharide.

2. Carbohydrate mixture according to claim 1, characterised in that
the mixing ratio a:b:c: is ca. 1:80:20.

3. Carbohydrate mixture according to claim 1, characterised in that it contains at least 5 wt % fucose.

4. Carbohydrate mixture according to claim 3, characterised in that it contains from 5 to 10 wt % fucose.

5. Carbohydrate mixture according to claim 1,
characterised in that
the fucose is bound to the oligosaccharides and polysaccharides as follows:
α1–2, α1–3, α1–4, α1–6.

6. Carbohydrate mixture according to claim 1,
characterised in that
it contains at least 1 wt % sialic acid(s) in free form and/or a form bound to an oligosaccharide and/or a polysaccharide.

7. Carbohydrate mixture according to claim 6,
characterised in that
it contains 1 to 5 wt % sialic acid(s).

8. Carbohydrate mixture according to claim 6 wherein the sialic acid(s) are in bound form as sialyllactose and/or disialyllactose or disialyllacto-N-tetraose.

9. Carbohydrate mixture according to claim 6
characterised in that the sialic acid(s) is (are) bound to the oligosaccharides as follows:
α2–3, α2–6, α2–8.

10. Carbohydrate mixture according to claim 1,
characterised in that
the monosaccharides essentially consist of the following monomers or the oligosaccharides and polysaccharides are essentially composed of the following monomers, which can be modified by —OSO3H and/or —OPO3H groups:
N-acetylnerminic acid, N-glycolyineuraminic acid and/or O-acerylated forms thereof, D-glucose, D-fructose, D-galactose, D-mannose, L-fucose, D-N-acetylglucosamine, D-N-acetylgalactosamine, D-xylose, L-rhamnose, D-arabinose, D-allose, D-talose, L-idose, D-ribose and monosaccharides with carboxyl groups.

11. Carbohydrate mixture according to claim 8 wherein the monosaccharide with a carboxyl group is D-galacturonic acid.

12. Carbohydrate mixture according to claim 1, characterised in that the monosaccharides, oligosaccharides and polysaccharides can be or have been fucosylated and optionally sialylated.

13. A method for prophylaxis and/or treatment of symptoms/diseases, which are connected with the association/adhesion of pathogenic substances and organisms to epithelia or other endogenous cells which comprises administering to an infant in need thereof the mixture of claim 1 in an amount of at least 100 mg/kg body weight/day.

14. A method for prophylaxis and/or treatment of symptoms/diseases, which are connected with the association/adhesion of pathogenic substances and organisms to epithelia or other endogenous cells which comprises administering to an infant in need thereof the mixture of claim 1 in an amount of about 500 mg/kg body weight/day.

15. A method for prophylaxis and/or treatment of symptoms/diseases, which are connected with the association/adhesion of pathogenic substances and organisms to epithella or other endogenous cells which comprises administering to an adult in need thereof the mixture of claim 1 in an amount of at least 200 mg/kg body weight/day.

16. A method for prophylaxis and/or treatment of symptoms/diseases, which are connected with the association/adhesion of pathogenic substances and organisms to epithelia or other endogenous cells which comprises administering to an adult in need thereof the mixture of claim 1 in an amount of about 1 g/kg body weight/day.

* * * * *